United States Patent [19]

Shum

[11] Patent Number: 5,252,759
[45] Date of Patent: Oct. 12, 1993

[54] PROCESS FOR PRODUCING OPTICALLY ACTIVE EPOXY ALCOHOL DERIVATIVES

[75] Inventor: Wilfred P. Shum, West Chester, Pa.

[73] Assignee: Arco Chemical Technology, L.P., Wilmington, Del.

[21] Appl. No.: 10,976

[22] Filed: Jan. 29, 1993

[51] Int. Cl.$^5$ .................. C07D 301/00; C07D 301/32; C07D 303/08; C07D 303/16

[52] U.S. Cl. .................. 549/541; 549/513; 549/556

[58] Field of Search .................. 549/513, 541, 556

[56] References Cited

U.S. PATENT DOCUMENTS

| | | | |
|---|---|---|---|
| 2,755,290 | 7/1956 | Mueller | 549/513 |
| 4,346,042 | 8/1982 | Baldwin et al. | 549/557 |
| 4,877,892 | 10/1989 | Brittelli | 549/552 |
| 4,946,974 | 8/1990 | Sharpless et al. | 549/551 |
| 5,084,582 | 1/1992 | Genet et al. | 549/513 |
| 5,136,062 | 8/1992 | Millar et al. | 549/513 |
| 5,145,974 | 9/1992 | Paul et al. | 549/513 |
| 5,153,338 | 10/1992 | Sharpless et al. | 549/551 |

FOREIGN PATENT DOCUMENTS

| | | |
|---|---|---|
| 3734219 | 4/1989 | Fed. Rep. of Germany . |
| 58-162570 | 9/1983 | Japan . |

OTHER PUBLICATIONS

Mesnard et al., "Effect of Tosyl Chloride on Monohydric Alcohols", *C. R. Acad. Sci.*, Nov. 13, 1963, pp. 2999–3001.

Klunder et al., "Arenesol Fonate Derivatives of Homochiral Glycidol: Versatile Chiral Building Blocks For Organic Synthesis", *J. Org. Chem.* 54, pp. 1295–1304 (1989).

Gao et al., "Catalytic Asymmetric Expoxidation and Kinetic Resolution: Modified Procedures Including in Situ Derivatization", *J. Am. Chem. Soc.* 109, pp. 5765–5780 (1987).

Klunder et al., "Asymmetric Epoxidation of Allyl Alcohol: Efficient Routes to Homochiral B-Adrenergic Blocking Agents", *J. Org. Chem.* 51, pp. 3710–3712 (1986).

Baldwin et al., "Synthesis of (R)- and (S)-Epichlorohydrin", *J. Org. Chem.* 43, pp. 4876–4878 (1978).

Chautemps et al., "Preparation de Sulfonates d'Alcools Ethyleniques et d'Epoxyalcools", *C. R. Acad. Sci. Ser. C.*, Feb. 26, 1968, pp. 622–644.

Nakabayashi et al., "Some Reactions of the Glycidyl Esters of Sulfonic Acids", *Bull. Chem. Soc. Japan* 39, pp. 413–417 (1966).

Szeija, "Synthesis of Sulfonic Esters Under Phase-Transfer Catalysed Conditions", *Synthesis*, Oct. 1979, pp. 822–823.

Czech. 148,516 (Abstract only); *Chem. Abstract* 79: 115310z)(1973).

*Primary Examiner*—Joseph E. Evans
*Attorney, Agent, or Firm*—Stephen D. Harper

[57] ABSTRACT

Organic sulfonate derivatives of optically active epoxy alcohols such as (R)- or (S)- glycidol are conveniently prepared from aqueous solutions of the epoxy alcohols.

20 Claims, No Drawings

PROCESS FOR PRODUCING OPTICALLY ACTIVE EPOXY ALCOHOL DERIVATIVES

FIELD OF THE INVENTION

This invention pertains to methods for the convenient preparation of organic derivatives of water-soluble optically active epoxy alcohols such as glycidol.

BACKGROUND OF THE INVENTION

Organic sulfonate derivatives of optically active (non-racemic) epoxy alcohols such as (R)- and (S)-glycidol are extremely useful and versatile intermediates in the synthesis of chiral drugs and other compounds having high physiological activity such as beta-blockers. The synthetic utility of such derivatives has been reviewed in Hanson, *Chemical Reviews* 91(4), 437–473 (1991).

One method known in the art for the preparation of these useful organic sulfonate derivatives is to react an optically active epoxy alcohol which has been previously isolated in pure form with an organic sulfonyl halide in the presence of a tertiary amine to take up the hydrogen halide generated. Such a procedure is described, for example, in Klunder et al., *Org. Chem.* 54, 1295-1304 (1989), Nakabayashi et al., *Bull Chem. Soc. Jpn.* 39, 413 (1966), and Chautemps et al., *C.R. Seances Acad. Sci., Ser. C,* Feb. 26, 1968, pp. 622-624. Practice of this method suffers from the disadvantage that the optically active epoxy alcohol to be reacted must first be obtained in sufficient purity so as to minimize the occurrence of undesired side reactions and to facilitate subsequent purification of the organic sulfonate derivative. Preliminary isolation of the optically active epoxy alcohol in this manner is not easily accomplished, however, due to the fact that many compounds of this type are notoriously unstable and reactive. Significant losses due to polymerization, ring-opening (e.g., hydrolysis or alcoholysis), acid-catalyzed or thermal decomposition, and the like are often encountered during purification of these substances. Recovery of non-crystalline water-soluble epoxy alcohols such as glycidol in high yield is especially difficult to achieve.

Another proposed solution to this problem is to carry the derivatization of optically active epoxy alcohols with organic sulfonyl halides in situ (without isolation of the epoxy alcohol) immediately following an asymmetric epoxidation reaction [see, for example, Gao et al., *J. Am. Chem. Soc.* 109, 5765 (1987)]. This derivatization method has the disadvantage, however, of providing relatively low isolated yields of the desired sulfonate derivatives when the stoichiometric ratio of epoxy alcohol organic sulfonyl halide is approximately 1:1. Another drawback of this proposed synthetic scheme is that a number of tedious purification or treatment steps before and after the derivatization reaction are still required. Without wishing to be bound by theory, it is believed that these problems are due, at least in part, to competing reactions of the organic sulfonyl halide with other protic species in the asymmetric epoxidation reaction mixture such as unreacted allylic alcohol, unreacted organic hydroperoxide, and the alcohol derived from the organic hydroperoxide. Another problem associated with the in situ derivatization method is that any unreacted organic hydroperoxide present must first be reduced using a reagent such as a trialkyl phosphate. Reductions of this type are extremely exothermic, however. Even under controlled conditions, a slight but significant loss of epoxy alcohol is difficult to avoid, especially on a large scale. Additionally, one must be careful not to use an excess of reducing agent since the sulfonyl halide or the desired organic sulfonate derivative may be reduced, leading to the production of sulfinate ester as a significant by-product.

The development of improved methods whereby organic sulfonate derivatives of optically active glycidol or the like may be obtained in high yield and high optical and chemical purity would therefore be of considerable value.

SUMMARY OF THE INVENTION

This invention provides a process for producing an organic sulfonate derivative of a water-soluble optically active epoxy alcohol comprising contacting an aqueous solution of the water soluble optically active epoxy alcohol with an organic sulfonyl halide in the presence of a tertiary amine for a time and at a temperature effective to form the organic sulfonate derivative.

The process of this invention efficiently affords high yields of sulfonate derivatives without the use of a large excess of organic sulfonyl halide and without any significant loss in optical purity during the derivatization and subsequent isolation steps. The favorable results obtained by practice of the instant process were quite surprising in view of the moisture sensitivity of organic sulfonyl halides in general, which readily undergo hydrolysis to yield the corresponding sulfonic acids. For example, Mesnard et al. in *C.R. Acad. Sci.,* pp. 2999–3001, Nov. 13, 1963, reported that the unreacted paratoluenesulfonyl chloride (tosyl chloride) present in a reaction mixture after contracting the tosyl chloride with a monohydric alcohol and pyridine under anhydrous conditions is readily hydrolyzed when water is added.

The discovery that an aqueous solution of an epoxy alcohol could be contacted with an organic sulfonyl halide to preferentially provide a sulfonic ester rather than a sulfonic acid was thus very much unexpected since water will typically be present in such solutions in large molar excess relative to the epoxy alcohol. In addition, contrary to expectation, the epoxide ring of the epoxy alcohol remains intact and is not hydrolyzed despite the presence of both water and a base (tertiary amine) during derivatization with the organic sulfonyl halide.

DETAILED DESCRIPTION OF THE INVENTION

Optically active epoxy alcohols which may be derivatized using the process of this invention include the class of organic compounds which containing both a hydroxyl group and an epoxide oxirane) group as well as a chiral center and which are soluble in or miscible with water. Preferably, such compounds have a solubility in water at 25° C. of at least 5 percent. Illustrative optically active epoxy alcohols include the optical isomers (enantiomers) of glycidol (also known as oxirane methanol), 2-methyl glycidol (2-methyl oxirane methanol), 3-methyl glycidol (3-methyl oxirane methanol), and the like. Such compounds may correspond to the general structure

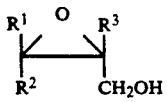

wherein one of $R^1$, $R^2$, and $R^3$ is methyl with the remaining R groups being hydrogen or wherein $R^1$, $R^2$, and $R^3$ are each hydrogen. The optically active epoxy alcohol may be enantiomerically enriched mixtures of R and S isomers wherein one isomer predominates or may be essentially optically pure (i.e., contain only a single isomer). Preferably, if a mixture is utilized, said mixture has an optical purity of at least 50% e.e. (enantiomeric excess) and more preferably has an optical purity of at least 70% e.e. As certain of the organic sulfonate derivatives readily recrystallize to higher optical purity, it may not always be necessary to start with an epoxy alcohol having extremely high optical purity in order to obtain a final derivative product which essentially contains only a single stereoisomer.

The aqueous solution of water soluble epoxy alcohol will typically be comprised of from 5 to 50 weight percent epoxy alcohol, with the balance being predominantly water. Minor amounts of other organic species such as alcohols and hydroperoxides may also be present, however, although the concentration of such species, especially those with active hydrogens, is preferably kept to a minimum (<5 weight % total). The aqueous solution to be processed in accordance with the present invention may be obtained by any of the conventional techniques known in the art for generating such a mixture.

One such method involves the reaction of an organic hydroperoxide with an allylic alcohol in the presence of a transition metal catalyst having a chiral ligand complexed with metal and an organic solvent, followed by extraction of the epoxy alcohol into an aqueous phase using water as an extractant. The organic hydroperoxide is typically a secondary or tertiary aliphatic or aromatic hydroperoxide such as t-butyl hydroperoxide, t-amyl hydroperoxide, cumene hydroperoxide, ethyl benzene hydroperoxide, cyclohexyl hydroperoxide, triphenylmethyl hydroperoxide, and the like. The allylic alcohol is selected such that it will yield the desired water-soluble optically active epoxy alcohol upon epoxidation and thus may be allyl alcohol, methallyl alcohol (2-methyl-2-propen-1-ol), 3-buten-1-ol, and the like. The transition metal in the catalyst is preferably selected from titanium, molybdenum, zirconium, vanadium, tantalum, and tungsten, with titanium having preferred due to its relatively high activity and stereoselectivity when complexed with a chiral ligand. Chiral carbinols represent a particularly preferred class of chiral ligands, including chiral (asymmetric) glycols (dihydroxy compounds) such as ester and amide derivatives of tartaric acid. The organic solvent is selected so as to provide rapid and stereoselective conversion of allylic alcohol to the optically active epoxy alcohol. Especially preferred solvents for use include halogenated hydrocarbons such as methylene chloride, dichloroethane, carbon tetrachloride, and the like, aliphatic hydrocarbons such as hexane, isooctane, cyclohexane, and the like, as well as aromatic hydrocarbons such as toluene, ethyl benzene, and cumene. Asymmetric epoxidation techniques are described in detail in the following publications, all of which are incorporated herein by reference in their entirety: Sheldon, *Aspects Homogeneous Catal.* 4, 3(1981); Jorgensen, *Chem. Dev.* 89, 431(1989); U.S. Pat. No. 4,471,130 (Katsuki et al.); U.S. Pat. No. 4,764,628 (Shum); U.S. Pat. No. 4,594,439 (Katsuki et al.); European Pat. Pub. No. 197,766; European Pat. Pub. No. 70,618; European Pat. Pub. No. 255,379; Pfenninger, *Synthesis* 89(1986); Gav et al. *J. Am. Chem. Soc.* 109, 5765(1987); Katsuki et al., *J. Am. Chem. Soc.* 102, 5974(1980); Finn et al. in *Asymmetric Synthesis*, Morrison, ed., Academic Press, N.Y.(1985), Vol. 5, Chapter 8, p.247; Rossiter in *Asymmetric Synthesis*, Morrison, ed., Academic Press, N.Y.(1985), Vol. 5, Chapter 7, p.193. The extraction of water soluble epoxy alcohols with water from an asymmetric epoxidation reaction mixture is described in detail in European Pat. Pub. No. 308,188, incorporated herein by reference in its entirety.

Yet another approach for obtaining a suitable aqueous solution of an epoxy alcohol is to carry out an asymmetric transformation catalyzed by a stereoselective enzyme in an organic solvent followed by water washing of the reaction mixture to remove the optically active epoxy alcohol. For example, isopropenyl and vinyl esters have been found to be useful for the lipase-catalyzed stereoselective acylation of racemic glycidol, affording a mixture of enantiomerically enriched glycidol and enantiomerically enriched glycidol ester [see Wang et al., *J. Am. Chem. Soc.* 110, 7200–7205 (1988)]. Another known method is to enantioselectively hydrolyze racemic carboxylic acid esters of epoxy alcohols with hydrolytic enzymes to provide chiral epoxy alcohol (which may be extracted from the reaction mixture with water into an aqueous phase) and chiral unhydrolyzed ester, as described in U.S. Pat. No. 4,732,853 (Whitesides et al.). Suitable epoxy alcohol aqueous solutions may also be obtained by subjecting a racemic mixture of R- and S- glycidol to the effect of an appropriate enantioselective oxidizing enzyme such as a alcohol dehydrogenase, as described, for example, in European Pat. Pub. No. 464,905.

Still another method for obtaining aqueous solutions of optically active epoxy alcohols suitable for use as the starting material in the process of this invention is the use of membrane technology as described, for example, in PCT Appl. No. WO 90-06996 (Lopez et al.), U.S. Pat. No. 4,800,162 (Matson), and U.S. Pat. No. 4,795,704 (Matson).

The aqueous solution of the water soluble optically active epoxy alcohol is contacted with an organic sulfonyl halide under conditions effective to form the desired organic sulfonate derivative. The choice of organic sulfonyl halide to be employed is not critical and may be selected so as to impart the desired properties to the organic sulfonate derivative. For example, the organic substituent attached to the sulfonyl halide functional group may contain electron-withdrawing moieties so as to facilitate the displacement of the sulfonate group formed in the derivative in a subsequent step such as nucleophilic reaction with an alkoxide or phenoxide. It is also well-known that certain organic sulfonate derivatives of optically active glycidol have the desirable property of recrystallizing to higher optical purity; such derivatives include glycidyl 4-chlorobenzene sulfonate, glycidyl tosylate, glycidyl 3-nitrobenzene sulfonate, and glycidyl 4-chloro-3-nitro benzene sulfonate (see U.S. Pat. Nos. 5,153,338 and 4,946,974). An especially useful class of suitable organic sulfonyl halides corresponds to the general structure $XSO_2R$ wherein X is Cl (chlorine) or Br (bromine) and R is selected from $C_1$–$C_{10}$ alkyl (e.g., methyl, ethyl, n-propyl, isopropyl, n-butyl, isobutyl, sec-butyl, tert-butyl, cyclohexyl and the like and substituted derivatives thereof including halogenated alkyl groups), $C_7$–$C_{20}$ aryl alkyl (e.g., benzyl, phenethyl, and the like and substituted derivatives thereof), and $C_6$–$C_{20}$ aryl (e.g., phenyl, naphthyl, and the like and substituted derivatives thereof including halogenated, alkylated, nitrated, and cyanated derivatives). Particularly preferred for use are organic sulfonyl halides having the general structure

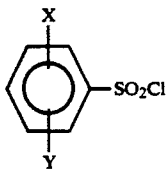

wherein X and Y are the same or different and are selected from hydrogen, $C_1$–$C_{10}$ alkyl (esp. methyl), halo (esp. Cl, F, and Br), and nitro ($NO_2$). Specific illustrative examples of such compounds include, but are not limited to, 2,4,6-trimethyl benzene sulfonyl chloride, methane sulfonyl chloride, trifluromethane sulfonyl chloride, trichloromethane sulfonyl chloride, tosyl chloride, 4-nitrobenzene sulfonyl chloride 3-nitrobenzene sulfonyl chloride, 2-nitrobenzene sulfonyl chloride, 4-chlorobenzene sulfonyl chloride, 4-chloro-3-nitrobenzene sulfonyl chloride, 4-bromobenzene sulfonyl chloride, 2,4,5-trichlorobenzene sulfonyl chloride, 2,4,6-triisopropyl benzene sulfonyl chloride, 4-methoxybenzene sulfonyl chloride, 2-naphthalene sulfonyl chloride, 1-naphthalene sulfonyl chloride, 2,4-dinitrobenzene sulfonyl chloride, 2-bromobenzene sulfonyl chloride, and 3-bromobenzene sulfonyl chloride.

The molar ratio of optically active epoxy alcohol to organic sulfonyl halide may desirably be in the range of from 0:5:1 to 1:0.5, but most preferably a slight excess (e.g., 5–20%) of the organic sulfonyl halide is utilized.

A tertiary amine is present during the reaction of the epoxy alcohol and organic sulfonyl halide to combine with the hydrogen halide generated during the reaction, thereby minimizing the acidity of the reaction mixture and permitting the desired derivatization to take place at a relatively low temperature so as to avoid any undesired decomposition of the epoxy alcohol or the organic sulfonate derivative. The tertiary amine is thus believed to function as a catalyst or promoter in the process of this invention. Suitable tertiary amines include the class of organic compounds of nitrogen that may be considered as derived from ammonia by replacing all three of the hydrogen atoms with hydrocarbon groups and may contain one or more tertiary amine groups. The tertiary amine may be monomeric, oligomeric, or polymeric in form. Examples of tertiary amines useful in the process of this invention include, but are not limited to, trimethyl amine, triethyl amine, pyridine, N,N-dimethyl aniline, triphenyl amine, 1,4-diazabicydo [2.2.2] octane (DABCO), $N,N,N^1,N^1$- tetramethyl ethylene dismine, and the like. Also suitable for use are ion exchange resins containing tertiary amine groups such as certain of the "Amberlite", "Amberlyst", and "Dowex" resins which are available commercially. In one embodiment of this invention, the tertiary amine is selected such that the amine hydrohalide salt formed during derivatization is water-soluble and is readily separated from the organic sulfonate derivative (which typically is water-insoluble) by washing with water.

The amount of tertiary amine utilized is advantageously adjusted so as to be approximately equal on a molar basis to the amount of organic sulfonyl halide, but an excess of tertiary amine could also be present if desired. Molar ratios of organic sulfonyl halide to tertiary amine of from 0:7:1 to 1:0.7 will typically be sufficient.

The organic sulfonyl halide is contacted with the epoxy alcohol for a time and at a temperature effective to form the desired organic sulfonate derivative by reaction of the hydroxy group of the epoxy alcohol so as to displace the halogen from the sulfonyl halide. The exact time and temperature utilized are not critical and will vary depending upon the reactivities and concentrations of the reaction components, among other factors, but typically contact times of from 1 minute to 12 hours and temperatures of from $-20°$ C. to $50°$ C. will suffice. The reaction temperature should not be so low as to cause the water present to freeze nor so high as to lead to the formation of undesired by-products.

The process of this invention may be performed on a batch, semi-batch, continuous or semi-continuous basis in any appropriately sized and configurated vessel capable of mixing the reaction components and maintaining the desired reaction temperature. In one preferred embodiment, the organic sulfonyl halide and the tertiary amine are first combined and the aqueous solution of epoxy alcohol subsequently added in an incremental fashion while providing good agitation of the mixture. In another embodiment, the organic sulfonyl halide is added to a mixture of the aqueous epoxy alcohol solution and tertiary amine. When the organic sulfonyl halide is water-insoluble or is a solid at the reaction temperature, the organic sulfonyl halide is preferably dissolved in an appropriate non-reactive solvent such as an aromatic hydrocarbon, halogenated aliphatic hydrocarbon; aliphatic hydrocarbon, ether, or the like.

Recovery, isolation, and further purification of the organic sulfonate derivative of the optically active epoxy alcohol may be accomplished by any appropriate method, which may vary depending upon the characteristics (e.g. solubility, melting point) of the derivative. Typically, the organic sulfonate derivative will be water-insoluble and thus can be readily separated from the amine hydrohalide salt generated and any unreacted epoxy alcohol by washing with water or other aqueous extractant. Where the organic sulfonate derivative is water-insoluble but soluble in a water-immiscible organic solvent, the derivative may be extracted into an organic phase using that organic solvent so as to leave the amine hydrohalide salt and any unreacted epoxy alcohol behind in an aqueous phase. The organic phase thus obtained may be further water-washed and then stripped of the organic solvent by distillation under vacuum to obtain the organic sulfonate derivative. If the organic sulfonate derivative has a melting point above ambient temperature, it may then be recrystallized from an appropriate solvent. Alternatively, the organic solvent may be selected such that it serves as a solvent to dissolve the organic sulfonate derivative during separation of the organic and aqueous phases but upon concentration and cooling of the separated organic phase also functions as a recrystallization medium. A second organic solvent in which the organic sulfonate derivative is less soluble may be added to enhance the recovery of the derivative in the crystallization step. The water-immiscible organic solvent may advantageously be present during the derivatization reaction; the derivative is thereby extracted into said organic solvent, which forms a separate phase from the aqueous solution of the epoxy alcohol, as the derivative is generated. In this embodiment of the invention, it has been surprisingly found that no phase transfer agent or catalyst need be added so as to accomplish the desired simultaneous derivatization and extraction. Alternatively, the solubility of the organic sulfonate derivative in the reaction mixture may be such that it precipitates from solution as it is formed. The precipitate (which may be in crystalline form) may either be collected in such precipitated form by any appropriate method such as filtration or may be extracted or dissolved into an appropriate solvent for recrystallization and/or washing. Suitable water-immiscible organic solvents for the above-identified purposes include, for example, aromatic hydrocarbons (e.g., benzene, toluene, ethylbenzene, chlorobenzene, and the like), aliphatic hydrocarbons (e.g., pentane, hexane, petroleum ether, isooctane, cyclohexane, methylene chloride, chloroform, tetrachloroethylene, and the like), esters, (e.g., ethyl acetate), ethers (e.g., diethyl ether), ketones (e.g., diethyl ketone), and the like. If the organic sulfonate derivative is a liquid at room temperature, purification methods such as fractional distillation, extraction, absorption, or preparative chromatography may be employed.

Without further elaboration, it is believed that one skilled in the art can, using the preceding description, utilize the present invention to its fullest extent. The following examples, therefore, as to be considered as merely illustrative and not limitative of the claims or remainder of the disclosure in any way whatsoever.

EXAMPLE 1

Technical grade 3-nitrobenzene sulfonyl chloride (10 g) was dissolved in toluene (60 g). The insoluble brown-colored solids present were removed by filterization. Triethylamine (4.6 g) was added to the organic sulfonyl chloride solution at 5° C., followed by an aqueous solution of optically active glycidol (16.65 g; 20 wt % glycidol) obtained by asymmetric epoxidation of allyl alcohol followed by water extraction of the epoxidation reaction mixture. After stirring for 2 hrs at 5° C. and 2 hrs at 25° C., the derivatization reaction mixture was combined with an additional quantity of toluene (33 g) to dissolve all of the precipitated glycidyl 3-nitrobenzene sulfonate and then washed with water (50 g). After phase separation, the top organic phase containing the organic sulfonate derivative was dried over anhydrous magnesium sulfate (10 g) and filtered. A portion of the organic phase (88 g) was distilled under vacuum at about 55° C. to remove toluene until the weight of the residue was about 16 g. At this point, crystallization of the glycidyl 3-nitrobenzene sulfonate was observed. Anhydrous ethanol (20 g) was then added and crystallization permitted to continue at room temperature with no stirring. Crystallization was completed by cooling to 50° C. over wet ice for another 30 minutes. The crystalline product was collected by filtration, washed with a small quantity of hexanes (5-10 g), and air-dried to yield 7.18 g of glycidyl 3-nitrobenzenesulfonate having a melting point of 58°-60° C. and an enantiomeric excess of at least 96% e.e. The overall yield was 61%.

EXAMPLE 3

Another 88 g portion of the organic phase obtained in Example 1 was treated in the same manner as described in Example 1 except that the magnesium sulfate treatment was omitted. Crystallization was initiated at 5° C. from a two-phase mixture after addition of methanol. The overall yield of the desired organic sulfonate derivative was 55% (6.50 g).

EXAMPLE 4

This example demonstrates that aqueous glycidol which has been kinetically resolved by lipase-catalyzed esterification can be used in the process of this invention to prepare glycidyl 3-nitrobenzenesulfonate having high optical purity.

A mixture containing racemic glycidol (20 g), vinyl acetate (18.5 g), lipase PS (2 g; an ester hydrolase derived from Pseudomanas sp and supplied by Amana), and cyclohexane (200 mL) was stirred at 23° C. The esterification was monitored by gas chromatography. At 65% glycidol conversion, the glycidol remaining in the reaction mixture had an e.e. of 52% as determined by a cyclodextrin-based capillary GC column. The lipase was removed by filtration and the filtrate washed with water (25 mL) to extract the resolved glycidol. The aqueous glycidol extract was subsequently used in the synthesis of (S)-glycidyl 3-nitrobenzene sulfonate as follows.

Technical grade 3-nitrobenzene sulfonyl chloride (20 g) was dissolved in toluene (120 g). The insoluble impurities were removed by filtration. The toluene solution was cooled to 5° C. and triethylamine (9.2 g) and the aqueous glycidol solution (ca. 20 wt. % glycidol) obtained as described above were then added to the toluene solution simultaneously. After stirring for 2 hours at 5° C. and 2 hours at 25° C., the reaction mixture was worked-up as described in Example 1. Crystallization of the organic sulfonate derivative from the concentrated reaction mixture was enhanced by the addition of 96% e.e. seed crystals of (S)-glycidyl 3-nitrobenzene sulfonate (0.2 g). The crystalline product was collected by filtration after crystallization was completed at 5° C. The (S)-glycidyl 3-nitrobenzene sulfonate had a melting point of 58°-60° C. and an e.e. of 96%, representing a substantial enrichment in optical purity over the kinetically resolved glycidol starting material.

EXAMPLES 5-15

The procedure of Example 1 is repeated using the following amounts of various organic sulfonyl halides in place of the 3-nitrobenzene sulfonate chloride.

| Example No. | Organic Sulfonyl Halide | Amt., g. | Expected Product |
| --- | --- | --- | --- |
| 5 | 4-chlorobenzene sulfonyl chloride | 9.5 | glycidyl 4-chlorobenzene sulfonate |
| 6 | 4-methylbenzene sulfonyl chloride | 8.6 | glycidyl 4-methylbenzene sulfonate |
| 7 | 4-nitrobenzene sulfonyl chloride | 10 | glycidyl 4-nitrobenzene sulfonate |
| 8 | 4-chloro-3-nitrobenzene sulfonyl chloride | 11.5 | glycidyl 4-chloro-3-nitrobenzene sulfonate |
| 9 | 4-bromobenzene sulfonyl chloride | 11.5 | glycidyl 4-bromobenzene sulfonate |
| 10 | 2,4,5-trichlorobenzene sulfonyl chloride | 12.6 | glycidyl 2,4,5-triclorobenzene sulfonate |
| 11 | 2,4,6-triisopropyl benzene sulfonyl chloride | 13.7 | glycidyl 2,4,6-triisopropyl benzene sulfonate |
| 12 | 4-methoxybenzene sulfonyl chloride | 9.3 | glycidyl 4-methoxybenzene sulfonate |
| 13 | 2-napthalene sulfonyl | 10.2 | glycidyl 2-naphtha- |

-continued

| Example No. | Organic Sulfonyl Halide | Amt., g. | Expected Product |
|---|---|---|---|
| | chloride | | lene sulfonate |
| 14 | 1-naphthalene sulfonyl chloride | 10.2 | glycidyl 1-naphthalene sulfonate |
| 15 | 2,4-dinitrobenzene sulfonyl chloride | 12.0 | glycidyl 2,4-dinitrobenzene sulfonate |

I claim:

1. A process for producing an organic sulfonate derivative of a water-soluble optically active epoxy alcohol comprising contacting an aqueous solution of the water-soluble optically active epoxy alcohol with an organic sulfonyl halide in the presence of a tertiary amine for a time and at a temperature effective to form the organic sulfonate derivative.

2. The process of claim 1 additionally comprising extracting the organic sulfonate derivative into an organic phase.

3. The process of claim 1 additionally comprising precipitating the organic sulfonate derivative from solution.

4. The process of claim 1 wherein the water-soluble optically active epoxy alcohol is selected from the group consisting of (R)-glycidol, (S)-glycidol, (R)-2-methyl glycidol, (S)-2-methyl-glycidol, (R)-3-methyl glycidol, (S)-3-methyl glycidol, and enantiomerically enriched mixtures thereof.

5. The process of claim 1 wherein the organic sulfonyl halide has the general structure

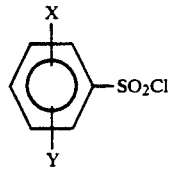

wherein X and Y are the same or different and are selected from hydrogen, $C_1-C_{10}$ alkyl, and nitro.

6. The process of claim 1 wherein the aqueous solution is obtained by extracting an asymmetric epoxidation reaction mixture comprised of the water-soluble optically active epoxy alcohol and a water-immiscible organic solvent with water.

7. The process of claim 1 wherein the molar ratio of water-soluble optically active epoxy alcohol to organic sulfonyl halide is from 0.5:1 to 1:0.5.

8. The process of claim 1 wherein the molar ratio of organic sulfonyl halide to tertiary amine is from 0.7:1 to 1:0.7.

9. The process of claim 1 wherein the water-soluble optically active epoxy alcohol is present in the aqueous solution at a concentration of from 5 to 50 weight percent.

10. The process of claim 1 wherein the temperature is from $-20°$ C. to $50°$ C.

11. The process for producing an organic sulfonate derivative of optically active glycidol comprising contacting an aqueous solution of the optically active glycidol with an organic sulfonyl halide having the general structure $XSO_2R$ wherein X is Cl or Br and R is selected from $C_1-C_{10}$ alkyl, $C_7-C_{20}$ aryl alkyl, and $C_6-C_{20}$ aryl in the presence of a tertiary amine at a temperature of from $-20°$ C. to $50°$ C. for a time effective to form the organic sulfonate derivative.

12. The process of claim 11 additionally comprising extracting said organic sulfonate derivative into an organic phase.

13. The process of claim 11 additionally comprising precipitating the organic sulfonate derivative from solution.

14. The process of claim 11 wherein X is Cl and R is a $C_6-C_{20}$ aryl group selected from methyl phenyl, 4-nitrophenyl, 3-nitrophenyl, 4-chlorophenyl, 4-chloro-3-nitrophenyl, 4-bromophenyl, 2,4,5-trichlorophenyl, 2,4,6-trisopropyl phenyl, 4-methoxyphenyl, 2-naphthyl, 2,4-dinitrophenyl, 2-mesityl, 1-naphthyl, 2-bromophenyl and 3-bromophenyl.

15. The process of claim 11 wherein the aqueous solution is obtained by extracting an asymmetric epoxidation reaction mixture comprised of the optically active glycidol and a water immiscible organic solvent with water.

16. The process of claim 11 wherein the aqueous solution is obtained by extracting an enzymatic kinetic resolution reaction mixture comprised of the optically active glycidol and a water immiscible organic solvent with water.

17. The process of claim 11 wherein the molar ratio of optically active glycidol to organic sulfonyl halide is from 0.5:1 to 1:0.5 and the molar ratio of organic sulfonyl halide to tertiary amine is from 0.7:1 to 1:0.7.

18. The process of claim 11 wherein the optically active glycidol is present in the aqueous solution at a concentration of from 5 to 50 weight percent.

19. The process of claim 11 wherein a water-immiscible organic solvent is additionally present during said contacting and the organic sulfonate derivative formed is extracted into the water-immiscible organic solvent.

20. The process of claim 19 wherein the organic sulfonate derivative is recovered from the water-immiscible organic solvent by crystallization.

* * * * *